US006213125B1

(12) United States Patent
Reese et al.

(10) Patent No.: US 6,213,125 B1
(45) Date of Patent: Apr. 10, 2001

(54) DEVICE FOR PROTECTING THE FACE OF A WEARER

(75) Inventors: George D. Reese, Fort Worth; Kevin K. Brunson, Argyle, both of TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/191,580

(22) Filed: Nov. 13, 1998

Related U.S. Application Data

(60) Provisional application No. 60/093,061, filed on Apr. 30, 1998.

(51) Int. Cl.$^7$ ....................................................... A61F 11/00
(52) U.S. Cl. ................................... 128/857; 128/858; 2/9
(58) Field of Search ............................. 128/845, 846, 128/857, 850; 2/9, 11, 15, 206

(56) References Cited

U.S. PATENT DOCUMENTS

| 4,635,628 | * | 1/1987 | Hubbard .......................... 128/201.17 |
| 5,099,525 | | 3/1992 | Millauro . | |
| 5,406,944 | | 4/1995 | Gazzara . | |
| 5,596,985 | | 1/1997 | Collier . | |
| 5,720,281 | | 2/1998 | Allen et al. . | |
| 5,803,075 | | 9/1998 | Yavitz . | |
| 6,026,511 | * | 2/2000 | Baumann ................................... 2/9 |

FOREIGN PATENT DOCUMENTS

| 0650712 A1 | 5/1995 | (EP) . |
| 0695774 A2 | 2/1996 | (EP) . |
| 2683153 A1 | 5/1993 | (FR) . |

OTHER PUBLICATIONS

PCT International Search Report dated Aug. 2, 1999 for International Application No. PCT/US99/09299, filed Apr. 29, 1999.

* cited by examiner

*Primary Examiner*—Michael A. Brown
(74) *Attorney, Agent, or Firm*—Dority & Manning, P.A.

(57) ABSTRACT

A device for protecting the face of a wearer is provided and includes a gas pervious mask dimensioned to fit over the nose and mouth of a wearer. A shield is coupled to the gas pervious mask. The shield is at least partially transparent over the eyes of the wearer. The shield is dimensioned to cover the gas pervious mask and the eyes of the wearer.

40 Claims, 10 Drawing Sheets

DEVICE FOR PROTECTING THE FACE OF A WEARER

RELATED APPLICATIONS

This is a continuing application claiming priority from U.S. Provisional Patent Application Ser. No. 60/093,061, filed Apr. 30, 1998 which is incorporated by reference for all purposes within this application.

BACKGROUND OF THE INVENTION

The present invention relates in general to the field of protective devices, and more particularly to a device for protecting the face of a wearer.

Protective devices allow people to live and work in a world that contains many dangerous conditions. For example, medical and dental care professionals are exposed to hazardous infectious pathogens on a daily basis. With the spread of acquired immune deficiency syndrome (AIDS) and other deadly diseases, the protection of these professionals from nasal and oral emissions, blood, and the like has become more critical than ever. Because each person's face includes regions of thin and penetrable membranes (e.g., eyes, nose, and mouth), this area is especially susceptible to contamination, and accordingly, should be afforded special protection from airborne contaminants and particulates.

Many face masks and protective devices have been developed in order to provide protection for the facial region. Typically, the devices designed to protect against splashed or sprayed liquids or other materials include a filter medium covering the nose and mouth of a wearer and may also incorporate a visor extending up from the filter medium to shield the wearer's eyes. In such devices, the bottom portion of the wearer's face is covered by the filter medium while the eyes and upper portion of the wearer's face are covered by a separate but attached plastic visor. One advantage of such devices is their integrated nature—one device fulfilling two separate functions.

However, such devices still do not solve all of the problems inherent in facial protection devices. Liquids are frequently sprayed or splashed towards the facial region of a wearer that may sometimes penetrate the layers of a facial mask or filtering medium subjecting the wearer to exposure. Masks and media have been developed which are somewhat successful in solving this problem by utilizing an increased number of layers or merely layers of thicker or treated material. However, such masks may not provide adequate protection for some operating environments and may prove uncomfortable to a wearer. Additionally, extra layers of thicker or treated materials add expense to the production of masks and can be impractical in an environment where disposable masks are required or preferred.

Devices incorporating a plastic visor to cover the upper portion of a wearer's face also fail to protect the wearer's skin exposed beneath the mask, for example, the neck region, from potentially hazardous fluids. This limitation has resulted in the misuse of such devices reducing their effectiveness; for example, a user may wear two devices simultaneously with the mask portions layered and one device upside down so that the inverted visor covers the region below the wearer's chin.

Accordingly, there is a need for an economical integrated device which can effectively shield a wearer from splashing or sprayed liquids and maintain wearer comfort.

SUMMARY OF THE INVENTION

The present invention recognizes and addresses the foregoing disadvantages, and others, of prior art construction and methods.

Accordingly, it is an object of the present invention to provide an improved design for a device for protecting the face of a wearer. Additional objects and advantages of the invention will be set forth in part in the following description, or may be obvious from the description, or may be learned through practice of the invention.

In accordance with the objects and purposes of the present invention, a device is provided for protecting the face of a wearer. The device includes a gas pervious mask body having dimensions to fit over the nose and mouth of the wearer. A shield, for example a transparent plastic member, may be coupled to the gas pervious mask and is dimensioned to extend over the eyes of the wearer and also to cover the gas pervious mask. The shield is preferably constructed of a liquid-impermeable and lightweight material. The mask component of the device may comprise any conventional mask body. For example, the mask may comprise a single layer of material, multiple layers of material, and multiple combinations of different materials. Various examples of the mask component are set forth in the following description.

The mask also includes devices for attaching to the face of the wearer. Any manner of conventional attaching devices are within the scope and spirit of the invention. For example, the mask may include at least one strap for securing about the wearer's head. Alternatively, the mask may include straps extending from the top and bottom edges of the body for being tied around the wearer's head. In an alternative embodiment, the mask may include loops for being fitted over the ears of a wearer. A vast number of attaching devices are well known to those skilled in the art and any manner of such device may be incorporated in the present invention.

The mask may also be configured as any number of conventional masks. For example, in one particular embodiment, the mask may be formed as a generally rectangular mask body and have a number of lateral pleats formed therein to allow the mask to conform to the nose and mouth of the wearer. Alternatively, the mask may be formed as a cup or cone shaped mask body, or may be formed from two trapezoidal panels sealed along three edges. Various configurations and shapes of the mask are well known to those skilled in the art and any and all such conventional masks are within the scope and spirit of the invention.

The shield component is preferably coupled or attached to the gas pervious mask at bonding areas. In one embodiment, bonding areas are located on the side edges of the mask. Alternatively, the bonding area may be located on the central front portion of the mask and the attaching straps of the mask may be connected with the outer side edges of the shield. In both configurations, the shield is flexible enough to also conform to the face of the wearer in generally the same manner as the mask conforms to the face.

In an alternative embodiment, a strip of plastic film or the like may be attached between the shield and the mask generally above the nose and mouth of the wearer. This strip acts as a vapor barrier to prevent moisture vapors from rising between the outside of the mask and the inside of the shield, which would have a tendency to fog the inside of the shield.

The shield itself can take on various configurations and shapes depending on use of the device. For example, it may be preferred to define a bottom edge of the shield with an arcuate shape so as to allow for more freedom of movement of the wearer's head. Also, the shield may incorporate lobe portions that extend above and behind the ears of the wearer. These lobes would cause the mask to conform around the sides of the wearer's head and thus protect the peripheral area of the wearer's eyes. In an alternative embodiment, the shield may also comprise two separate shield portions attached to the mask in an overlying fashion. This embodiment may allow for more flexibility and movement of the shields.

It should be appreciated that a number of configurations and alternative embodiments may be employed in the present invention, and that the invention is not limited to any particular type of mask.

The accompanying drawings, which are incorporated in and constitute a part of this specification, illustrate a number of embodiments of the invention and, together with the description, serve to explain the principles of the invention.

BRIEF DESCRIPTION OF THE DRAWINGS

A full and enabling disclosure of the present invention, including the best mode thereof and directed to one of ordinary skill in the art, is set forth in this specification, which makes reference to the appended drawings, in which.

DETAILED DESCRIPTION OF THE PREFERRED EMBODIMENTS

Reference will now be made in detail to the presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention cover such modifications and variations as come within the scope of the appended claims and their equivalents.

Figure 1:
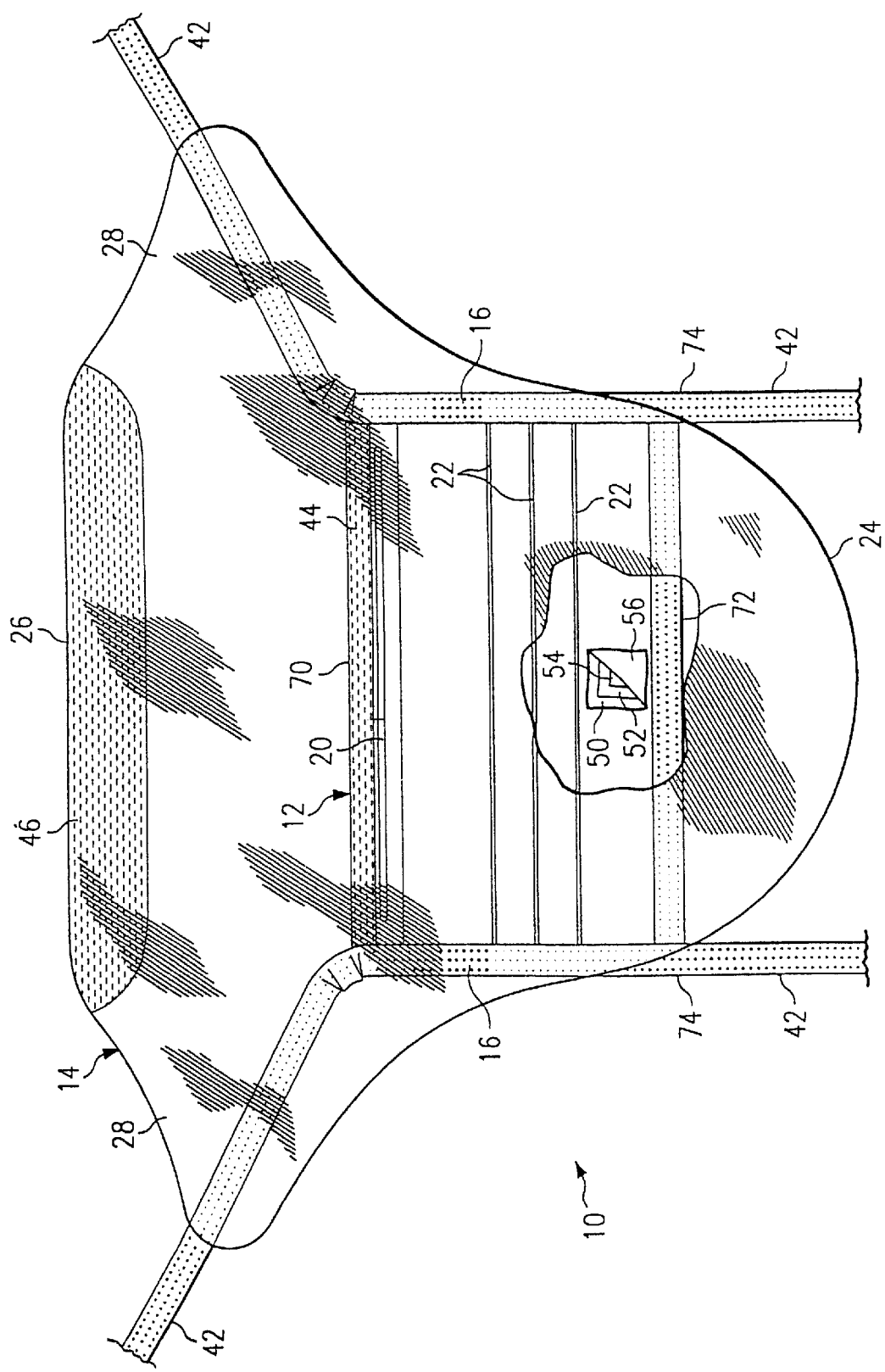
FIG. 1 is a front elevational view with a cutaway portion of one embodiment of a device for protecting the face of a wearer, designed in accordance with the present invention.

FIG. 1 shows a front elevational view of a device 10 for protecting the face of a wearer constructed in accordance with the present invention. Protective device 10 includes a gas pervious mask 12 coupled with a shield 14 at bond areas 16. Shield 14 is dimensioned to completely cover the surface of mask 12 and may extend beneath the mask 12. Gas pervious mask 12 has at least one tie strap 42 for securing protective device 10.

Illustrating a preferred embodiment, mask 12 in FIG. 1 is an improved filter mask having a filter medium with lateral pleats 22 and a malleable strip 20 parallel to and in the vicinity of pleats 22. Top edge 70, bottom edge 72, and side edges 74 cooperate with each other to define the periphery of the body of mask 12 that contacts the face of the wearer. Malleable strip 20 is preferably positioned in the center of a top edge 70 of mask 12 and has a length in the range of fifty percent (50%) to seventy percent (70%) of the total length of top edge 70. Malleable strip 20 may be manufactured from quarter-tempered aluminum with a rectangular cross section to enhance performance of mask 12 and closely fit the mask to the nose and cheeks of the wearer. Malleable strip 20 may also be formed from molded or malleable steel or plastic or any other suitable material that can be conformed to a wearer's face.

Lateral pleats 22 allow expansion of mask 12 to cover the mouth and nose of a wearer. The number, size, and orientation of pleats 22 formed in mask 12 may be varied to provide the desired fit with the face of the wearer and to conform to the specific environment in which the mask is to be used. The operation of pleats 22 supports mask 12 away from the nose and mouth of the wearer, thereby providing greater filtering efficiency and wearer comfort. Such a mask is described in U.S. Pat. No. 4,635,628, issued to Hubbard et al. on Jan. 13, 1987, the entire disclosure of which is hereby incorporated by reference.

Figure 2:
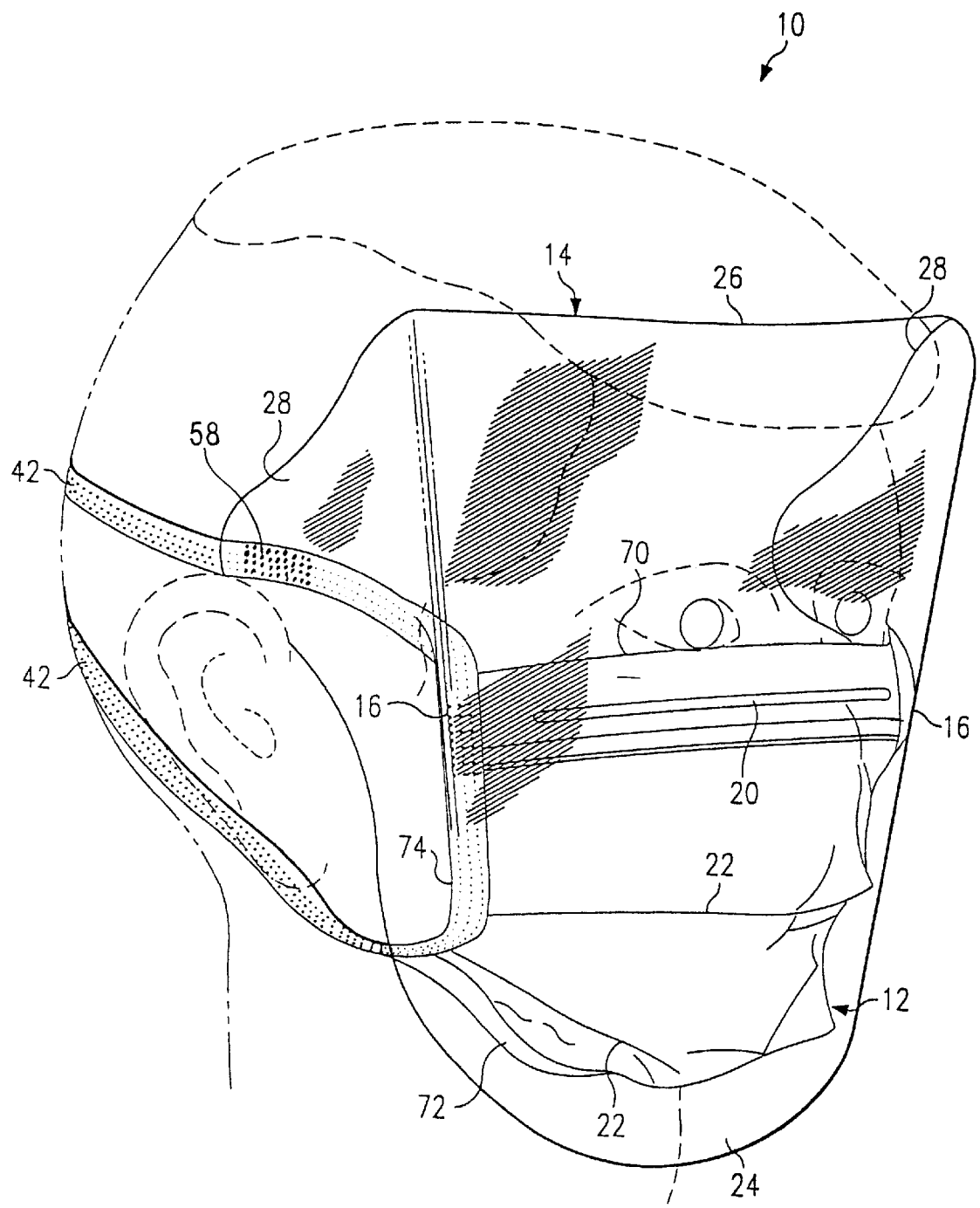
FIG. 2 is a perspective view of the protective device shown in FIG. 1, placed about the face of a wearer.

FIG. 2 is a perspective view of the protective device shown in FIG. 1, placed about the face of a wearer. In this embodiment, protective device 10 includes a pleated-style gas pervious mask 12 and a shield 14. FIG. 2 clearly illustrates that mask 12 includes a body portion that is dimensioned to fit over the nose and mouth of a wearer. Mask 12 allows a wearer to breath through the material of mask 12, while shielding the nose and mouth from airborne contaminants.

Top edge 70 with malleable strip 20 conforms very closely to the configuration of the nose and cheeks of the wearer. It is important that bottom edge 72 fits closely with the chin of wearer and top edge 70 fits closely with the nose and cheeks of wearer 12 to prevent bypass or blow-by of fluids either entering mask 12 or being discharged from mask 12 during use by wearer.

Figure 11:
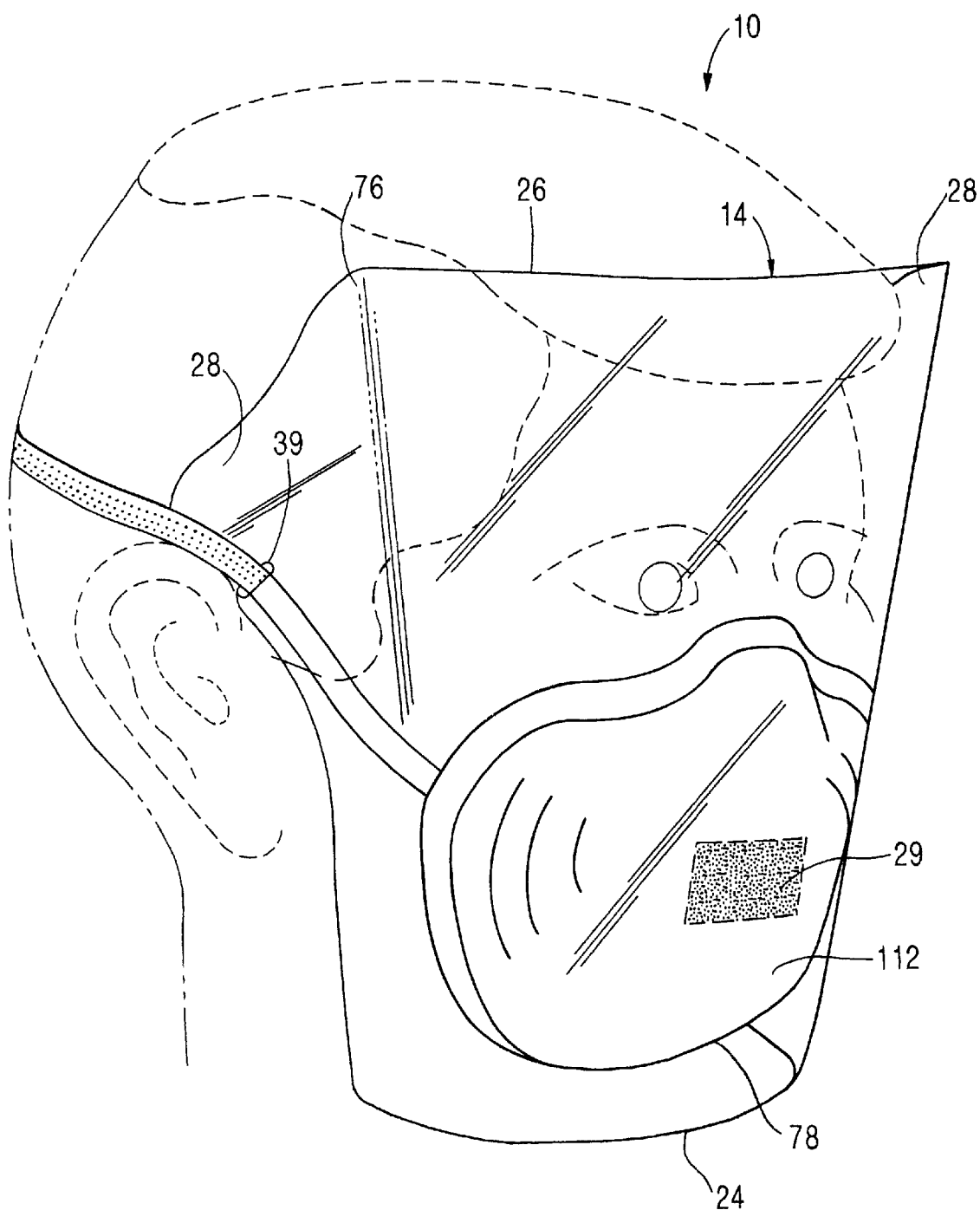
FIG. 11 is a perspective view of one embodiment of a protective device designed in accordance with the present invention, placed about the face of a wearer.

In another embodiment, mask 112 may be a traditional cup or cone-shaped mask as shown in FIG. 11. Cone mask 112 may be formed from molded plastic or the like shaped to conform closely around the nose and mouth or chin of the wearer. Such cone masks are well-known in the art and are described in U.S. Pat. No. 4,384,577, issued to Huber et al. on May 24, 1983; U.S. Pat. No. 4,454,881, issued to Huber et el. on Jun. 19, 1984; and U.S. Pat. No. 4,600,002, issued to Maryyanek et al. on Jul. 15, 1986; the entire disclosure of each being hereby incorporated by reference.

Figure 12:
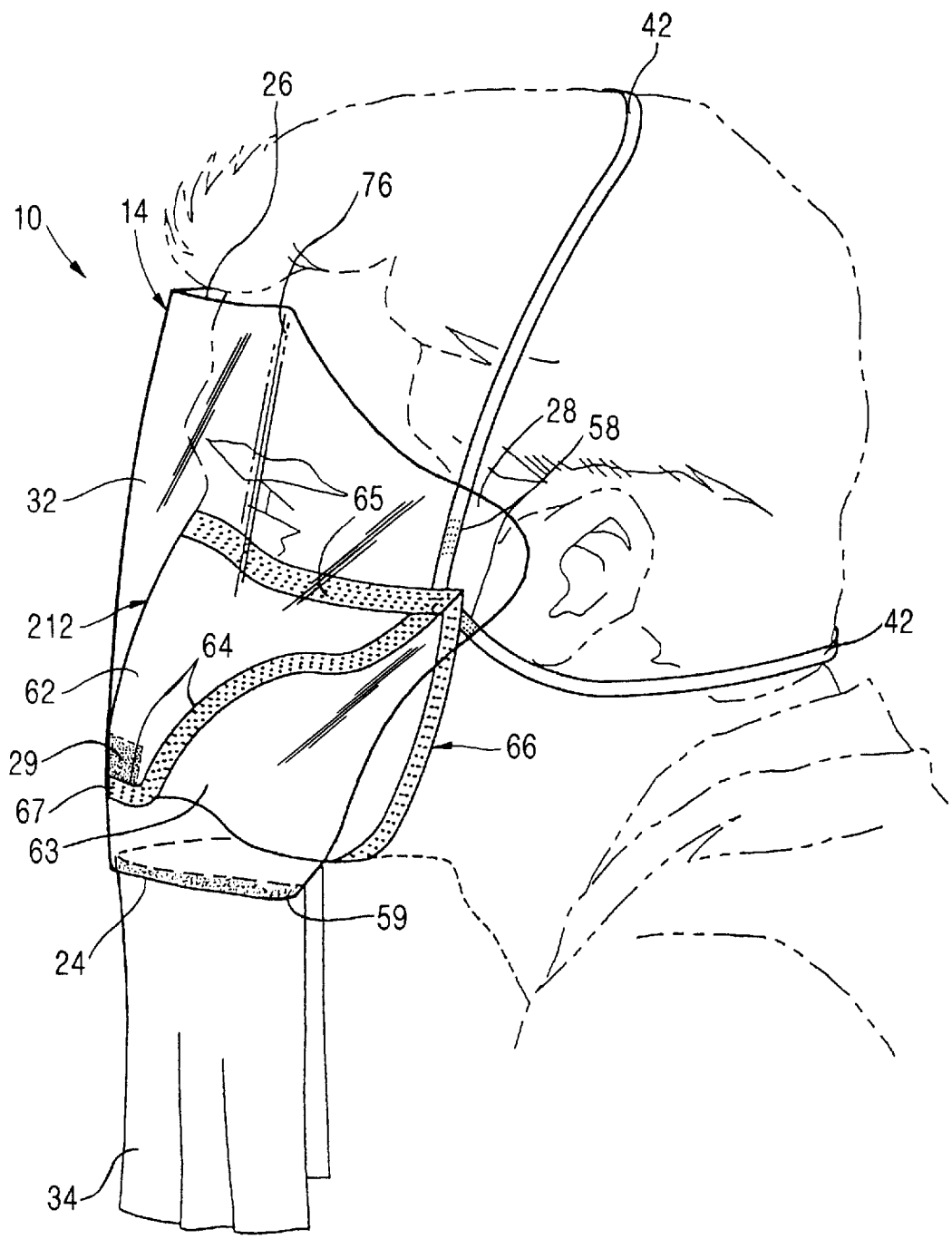
FIG. 12 is a perspective view of one embodiment of a protective device designed in accordance with the present invention, placed about the face of a wearer.

In another embodiment shown in FIG. 12, the body of mask 212 may be formed from two panels 62,63 of generally trapezoidal shape, sealed along three edges 64, with the longest edge of each of the upper and lower panels forming an opening 66, to extend around a wearer's nose and mouth. Paneled mask 212 may include a malleable strip 20, described above, along the unsealed edge 65 of its upper panel 62 for conforming the panel around the nose of the wearer. As can be seen in FIG. 12, the trapezoidal shape of the upper and lower panels 62,63 allow mask 212 to remain off the face of the wearer when in use. The shaping also facilitates opening 66 to conform to the nose, cheeks, and chin of the wearer. Such a mask is described in U.S. Pat. No. 5,322,061, issued to Brunson on Jun. 21, 1994, the entire disclosure of which is hereby incorporated by reference.

In one embodiment, mask 12 may be composed of multiple layers of material. As shown in FIG. 1, these layers include a first layer 50, a second layer 52, a third layer 54, and a fourth layer 56. An example of such a mask is described in U.S. Pat. No. 4,920,960 issued to Hubbard et al. on May 1, 1990, the entire disclosure of which is hereby incorporated by reference.

In one embodiment, the first or innermost layer 50 is designed to prevent unwanted materials such as facial hair, loose fibers or beads of perspiration from contacting the next outermost layer which could cause a wicking effect to draw liquids therethrough. Innermost layer 50 also provides a comfortable surface for contact with the face of the wearer. Innermost layer 50 of mask 12 may be constructed of a lightweight, highly porous, softened, non-irritating, non-woven fabric, such as, for example, Dexter, Inc. Product No. 3768.

The second layer 52 may comprise a barrier material that is capable of differentiating between gases and liquids and may be constructed from, for example, Visqueen Film Products low density polyethylene VISPORE X-6212. The barrier material is designed to freely pass gases in either direction while restricting the passage of liquids in at least one direction. When used in the mask, the barrier material restricts the passage of external fluids and particulates to the nose and mouth of the wearer.

The third layer 54 may be formed from a filtration media such as melt-blown polypropylene or polyester. This filtration media inhibits the passage of airborne bacteria in either direction, thereby preventing passage of germs and pathogens to and from the nose and mouth of the wearer.

The fourth or outermost layer 56 may comprise a treated cover stock such as cellulose fiber or other non-woven material. The cover stock may be chemically coated or treated, for example, by spraying with a liquid repellant, to render the cover stock resistant to liquids. The cover stock of the outermost layer cooperates with the filtration media of third layer 54 and the barrier material of second layer 52 to impede any liquid that may be splashed, sprayed or thrown at mask 12. Thus, the multi-layer construction of mask 12 provides the wearer with reliable protection from airborne particulates.

In one embodiment, one or more layers of material may extend beyond the bottom edge of the mask to form a neck guard (not shown) for the wearer. The choice of layer or layers for the wearer would depend upon the environment in which the mask is to be used and any combination of such materials and shape of the mask are contemplated within the scope and spirit of the invention.

Layers 50, 52, 54, and 56 may be bonded to each other, for example, in a generally rectangular configuration. Such bonding is preferably provided along top edge 70, a bottom edge 72 and side edges 74, respectively. The process by which the bonding is formed may comprise any one or a combination of sewing, gluing, heat sealing, welding, ultrasonic bonding and/or any other suitable bonding procedure.

Although mask 12 in one preferred embodiment has been described as comprising four layers of material, it should be understood that in other embodiments mask 12 may comprise greater or fewer numbers of layers of material. For example, because shield 14 prevents airborne particulates from contacting mask 12 or reaching the face of the wearer as described below, the present invention contemplates that, in an alternative embodiment, the outermost layer 56 comprising treated cover stock may be omitted from mask 12. Moreover, for some applications, a single layer of material may comprise the filter medium of mask 12. With still other applications, mask 12 can be constructed of thinner, more porous material that is conducive to easier breathing and enhanced ventilation.

With further reference to FIG. 1, shield 14 is of an appropriate size to protect substantially the entire facial region of an average adult. Shield 14 is coupled to mask 12 so that the lower portion of shield 14 substantially covers mask 12. In other embodiments, protective device 10 may include a shield 14 of smaller or larger size when necessary to best perform its specific function. Shield 14 is preferably flat to facilitate ease of manufacture, shipping, storage, and disposal. Shield 14 may be constructed of any transparent, liquid-impermeable and lightweight material, such as polyester, polycarbonate, and the like. Shield 14 is also preferably disposable to prevent the possible spread of any contaminants through cleaning procedures or future reuse.

Shield 14 is either entirely transparent or includes a transparent portion to allow a wearer to see through shield 14 in order to perform necessary tasks. Shield 14 is dimensioned to cover the face of a wearer, more specifically shield 14 is dimensioned to cover gas pervious mask 12 and the eyes of a wearer. The length of shield 14 preferably extends the length of wearer's face, and the width of shield 14 is sufficient to substantially enclose the wearer's face. Shield 14 is coupled to mask 12 so that shield's lower portion completely covers mask 12 and extends beyond the wearer's chin. Thus, the perimeter of shield 14 extends beyond the perimeter of underlying gas pervious mask 12. Shield 14 may also include arcuate lobes for shielding the eyes of a wearer.

In a preferred embodiment, shield 14 has an arcuate bottom edge 24, a flat top edge 26, and two arcuate lobes 28 extending from either side of the shield. The arcuate bottom edge's curvature prevents shield 14 from interfering with head movement and clothing of the wearer while still allowing for substantial coverage of the face of the wearer. Arcuate lobes 28 are preferably formed as an integral part of and extend from main body 80 of shield 14. Arcuate lobes 28 provide extended frontal and lateral coverage of the temple region of the wearer to better protect the eyes of the wearer from liquid spray or liquid splash. Shield 14 is preferably scored or creased to allow flexible movement of the arcuate lobes 28. Thus, arcuate lobes 28 may be folded back to protect the eyes of the wearer. In another embodiment illustrated in FIG. 4, shield 14 is formed with similarly shaped lobes 38 extending from each side of curved top 26, and includes a flat bottom edge.

Figure 3:
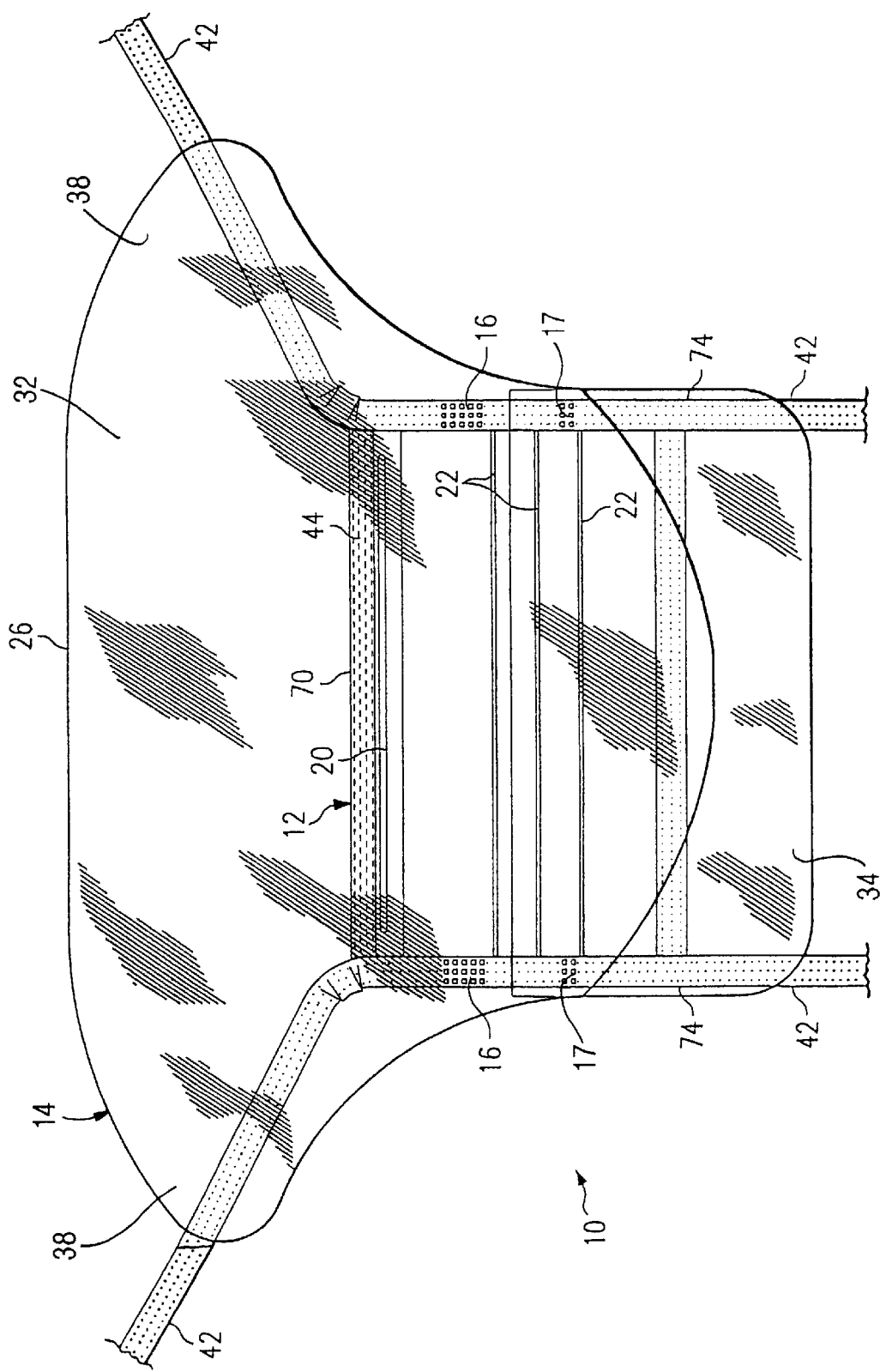
FIG. 3 is a front elevational view of one embodiment of a device for protecting the face of a wearer designed in accordance with the present invention.
Figure 6:
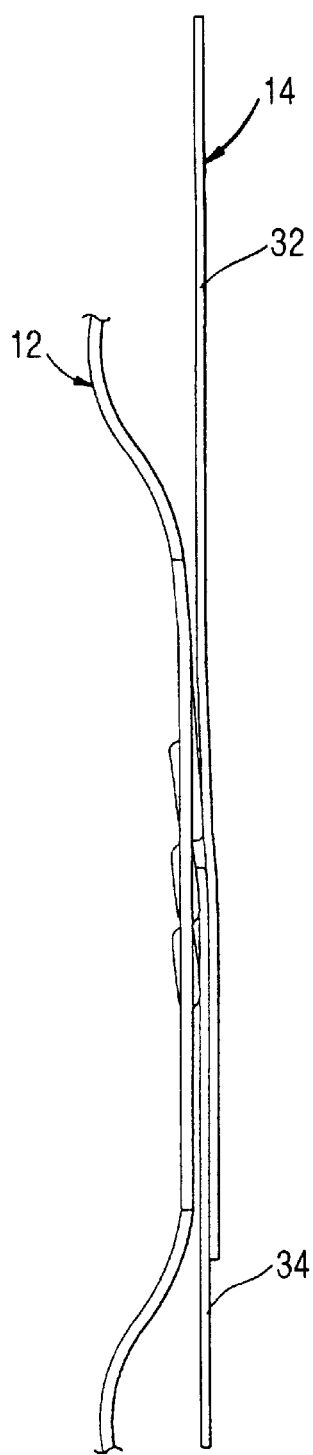
FIG. 6 is a side view of a portion of the protective device shown in FIG. 3.

As illustrated in FIG. 3, shield 14 may include two parts, an upper portion 32 overlapping a lower portion 34. Upper portion 32 is attached to the mask 12 at bond points 16 and lower portion 34 is attached at bond points 17. This arrangement is more specifically illustrated in FIG. 6. The upper and lower portions may be constructed from different materials, for instance, lower portion 34 need not be transparent because it does not cover the eyes of the wearer. Lower portion 34 may be constructed from a less rigid material for improved fit and more freedom of movement.

Figure 9:
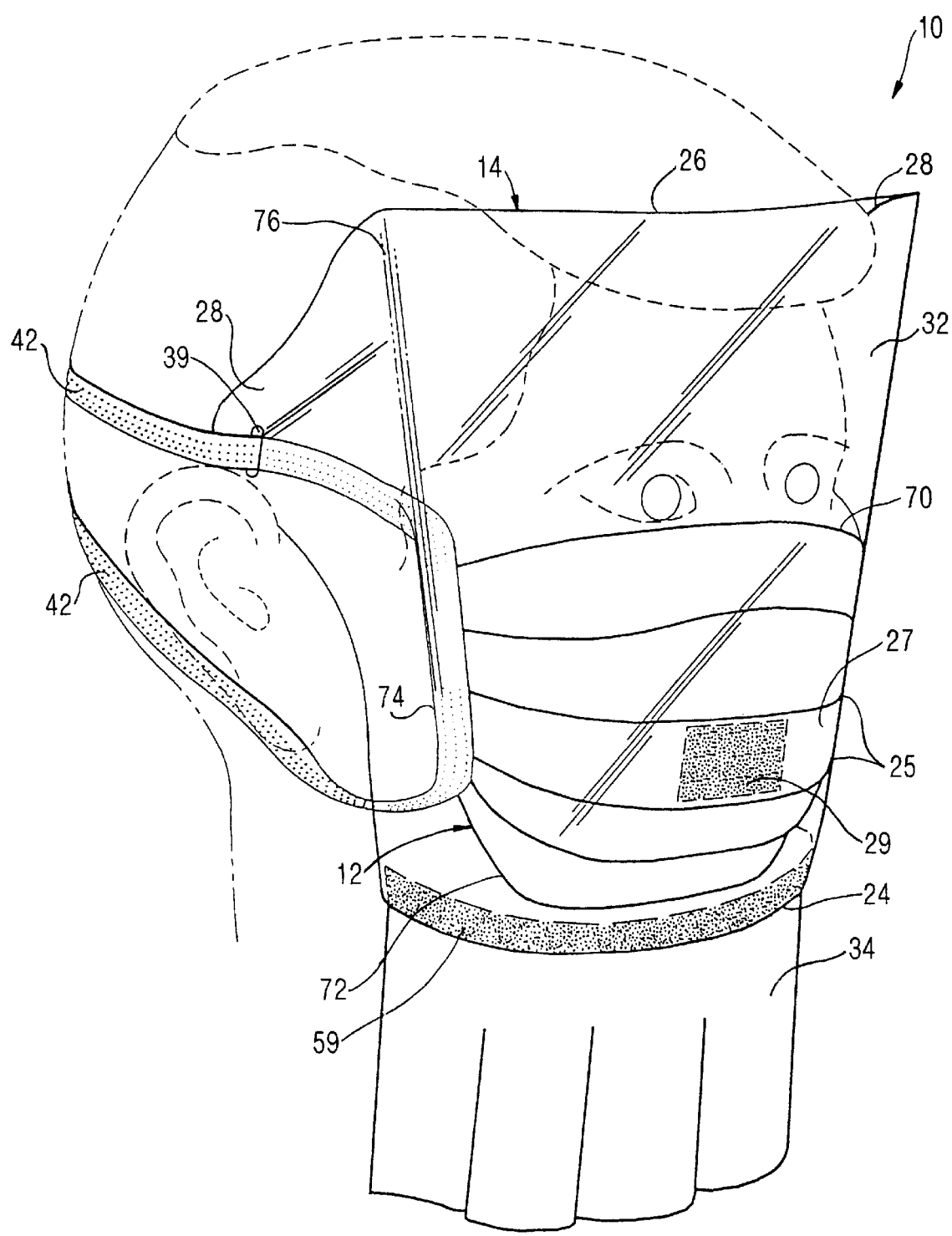
FIG. 9 is a perspective view of one embodiment of a protective device designed in accordance with the present invention, placed about the face of a wearer.

FIGS. 9 and 12 illustrate alternate embodiments of protective device 10, each with a lower portion 34 incorporating a draping material. FIGS. 9 and 12 also illustrate embodiments in which the lower portion 34 of shield 14 is attached to the upper portion 32, rather than to the mask 212, at an elongated bond area 59. Alternatively, the bond could be created at numerous points along the bottom edge 24 of the upper portion 32.

Shield 14 may incorporate a non-reflective surface 46 positioned along, for example, a top edge 26 of shield 14 as illustrated in FIG. 1. Non-reflective surface 46 functions to reduce the amount of overhead light shining directly into the wearer's eyes. Non-reflective surface 46 may be fabricated by printing a dark color onto the desired location of shield 14 by known processes. Non-reflective surface 46 may also be formed by laminating or otherwise affixing a dark colored strip of vinyl to the shield. The resultant darkened strip may be opaque or translucent. Alternatively, non-reflective surface 46 may be formed by mechanical or chemical etching. Mask 12 may also incorporate a darkened strip 44 along top edge 70 of mask 12 to further reduce glare associated with overhead lighting.

In one embodiment, as shown in FIGS. 4, 5, 7, and 8, a strip of anti-fogging material 36 may be positioned between shield 14 and mask 12 to prevent the rise of vapors which have a tendency to create fog on shield 14. The anti-fogging strip 36 may be a strip of plastic film. As in FIGS. 4, 7, and 8, strip 36 may be attached to both mask 12 and shield 14 with any conventional adhesive or other suitable attaching means. Alternatively, the anti-fog strip 36 may be positioned inside mask 12 and attached to top edge 70 of mask 12 to be worn between mask 12 and the face of the wearer shown in FIG. 5.

Figure 4:
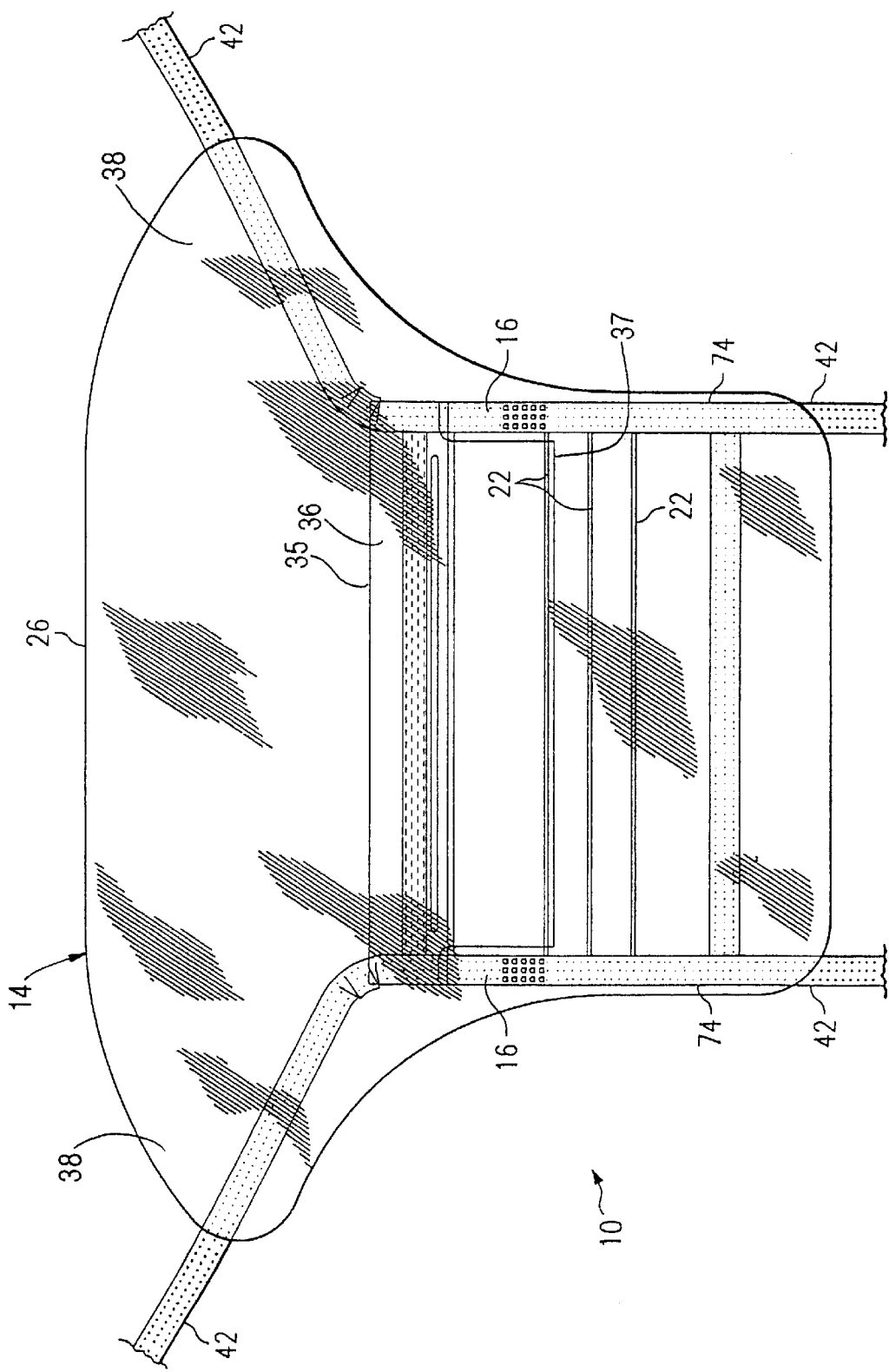
FIG. 4 is a front elevational view of one embodiment of a device for protecting the face of a wearer designed in accordance with the present invention.

As illustrated in FIG. 4, anti-fogging strip 36 may be connected to mask 12 and shield 14 along the front edge 35 and the back edge 37 of strip 36, respectively. In one embodiment shown in FIG. 5, anti-fogging strip may be bonded along with mask and shield 14 at bond areas 16. Top edge 40 and bottom edge 33 of strip 36 may or may not be attached to mask 12 and shield 14.

In some environments, it is desirable for strip 36 to hold shield 14 away from mask 12, such as when the wearer must wear eyeglasses. A distance between mask 12 and shield 14 also serves to create a cooler environment for the wearer and to increase breathability. Strip 36 may be constructed from material imparting malleability to create distance between mask 12 and shield 14. In such a configuration, it may be desirable for strip 36 to be constructed from material designed to allow heat to escape upward.

Figure 7:
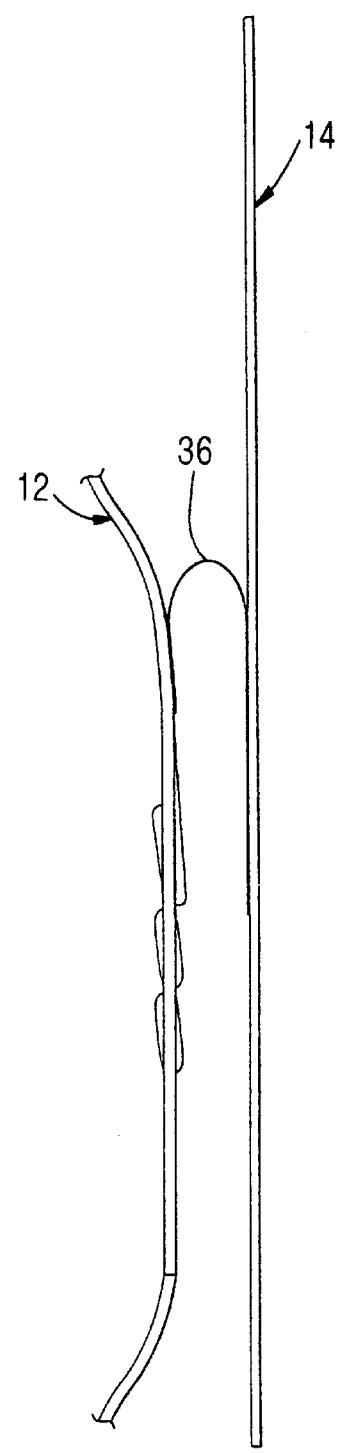
FIG. 7 is a side view of a portion of one embodiment of the protective device shown in FIG. 4.
Figure 8:
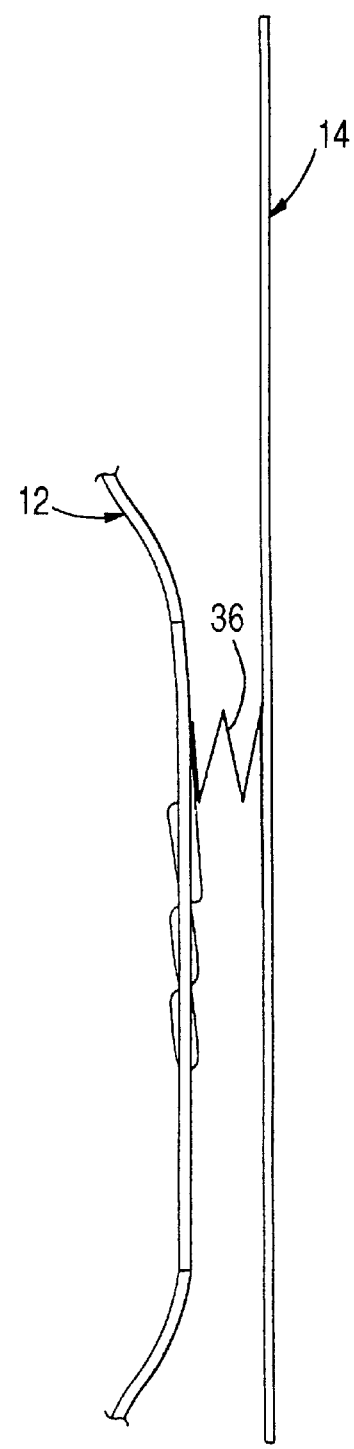
FIG. 8 is a side view of a portion of one embodiment of the protective device shown in FIG. 4.

In one embodiment illustrated in FIG. 7, anti-fogging strip is attached between mask 12 and shield 14 in a folded configuration. FIG. 8 illustrates an embodiment in which anti-fogging strip is positioned between mask 12 and shield 14 in a pleated or corrugated configuration.

Shield 14 is preferably attached to mask 12 in such a way as not to inhibit the ability of mask 12 to conform to a wearer's face as described above. One way of attachment that allows mask 12 to effectively conform to the face of a wearer is to attach shield 14 to the body of gas pervious mask 12 only at bond areas 16 on side edges 74 of mask 12. Bond areas 16 are positioned on the upper portion of side edges 74 so that they couple the mask 12 to the shield 14 approximately midway between shield's bottom edge 24 and top edge 26. Bond areas 16 may be formed by any one or a combination of known techniques, including mechanical snaps, adhesive attachments, pressure sealing, ultrasonic sealing and heat sealing.

Preferably, bond areas 16 are of a predetermined area and only of sufficient size (approximately ¼ inch by ½ inch) to secure shield 14 to mask 12. It has been found that both mask 12 and shield 14 more easily adapt to the contours of the face of the wearer if bond areas 16 do not extend along the entire length of side edges 74 of mask 12. If bond areas 16 were to extend farther along mask 12 holding shield 14, the likelihood of creasing shield 14 would increase, as a wearer might attempt to bend shield 14 to conform with curvature of the mask. Limiting bond areas 16 to only a portion of the length of side edges 74 thus provides the necessary flexibility to conform mask 12 to the facial contours of each individual wearer. Additionally, such a bonding structure allows malleable strip 20 of gas pervious mask 12 sufficient latitude to conform to the wearer's nose and cheeks.

Figure 10:
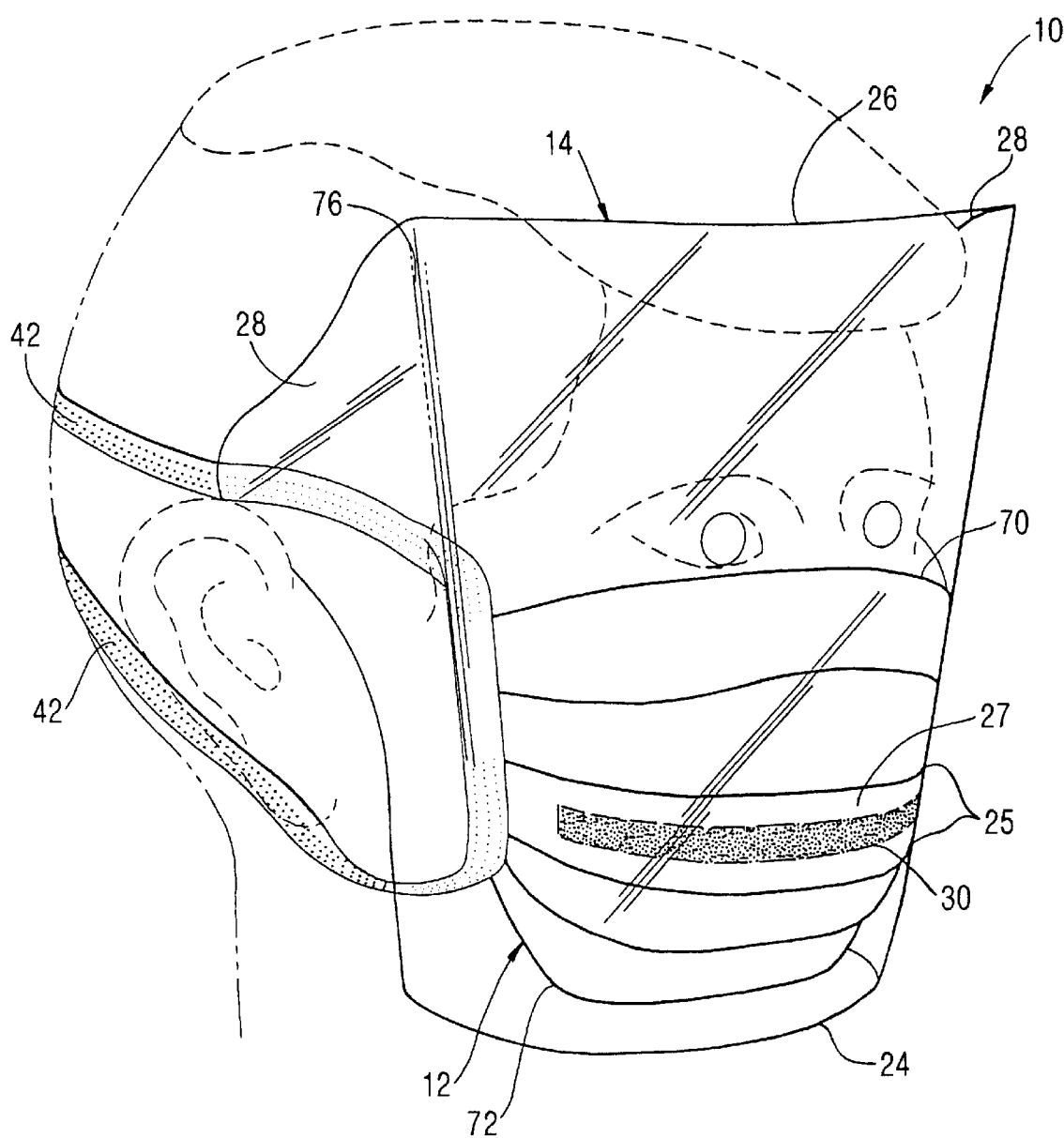
FIG. 10 is a perspective view of one embodiment of a protective device designed in accordance with the present invention, placed about the face of a wearer.

In an alternative embodiment, shield 14 may be attached to the outermost part of underlying mask 12. FIGS. 9 and 10 illustrate such an attachment where mask 12 is a pleated-style mask. In this configuration, complementary inverted pleats 26 form a center gusset 27, providing an attachment surface for shield 14. FIG. 9 shows one embodiment of the attachment with a rectangular centrally located bond area 29. FIG. 10 shows an alternate embodiment with an elongated bond area 30.

Bond areas 29,30 may be formed by any one or a combination of known techniques, including adhesive attachments, pressure sealing, ultrasonic sealing and heat sealing.

Both FIGS. 9 and 10 depict shield 14 with creases 76 positioned just beyond side edges 74 of mask 12. Creases 76 permit the lobes 28 of shield 14 to wrap around the wearer's head without dislocating mask 12, providing increased protection for the wearer's eyes. Creases 76 in shield 14 may be preferred for single bond area devices as well as for devices incorporating off-the-face style masks.

As discussed above, protective device 10 may utilize a non-pleated off-the-face style mask such as the traditional cone mask shown in FIG. 11 or the trapezoidal paneled mask shown in FIG. 12. The embodiment of protective device 10 shown in FIG. 11 includes a cone-style mask 12 with a single bonding area 29 to shield 14 that is centrally located on the outer surface of mask 12.

Shield 14 may extend beyond the bottom edge 78 of cone mask 12 and may include a pre-creased portion 76 along lobes 28 illustrated in FIG. 11. FIG. 12 illustrates an embodiment of protective device 10 incorporating paneled mask 212, discussed above. Paneled mask 212 is attached to shield 14 at a single bonding area located along the center seam 67 of mask 212.

Mask 12 may be secured to a wearer's face by at least one set of tie straps 42 as illustrated in FIGS. 2,9,10,11 and 12. Tie straps 42 may be formed from various types of material. In an embodiment of the present invention, tie straps 42 are preferably formed from thermally bonded polypropylene having a basis weight of 1.5 to 1.65 ounces per square yard. This particular type of material can be ultrasonically welded, stitched or heat and pressure bonded in various patterns to provide a resilient means for use in attaching mask 12 to the face of the wearer.

Alternative means of securing mask 12 to wearer's face may also be utilized. For example, ear loops may be attached to the body of mask 12 such as those disclosed in U.S. Pat. No. 4,941,470, issued to Hubbard et al. on Jul. 17, 1990, the complete disclosure of which is hereby incorporated by reference. In other applications, securing members may be used which consist of straps constructed from polyurethane, elastic rubber, or a covered stretch yarn. The covered stretch yarn may consist of an elastomeric material wrapped with nylon or a polyester. For other applications double knitted headbands such as circle knitted polyester/LYCRA or nylon/LYCRA can be utilized.

In the embodiment illustrated in FIG. 2 incorporating a pleated-style mask, tie straps 42 are shown originating from each of the four corners of the body of mask 12 and capable of being tied securely around the head of the wearer. The arrangement of tie straps 42 is such that straps 42 extending from top edge 70 may be placed over the top of the head of wearer 12. Straps 42 extending from bottom edge 72 may be positioned around the lower base of the head of the wearer. Tie straps 42 may be positioned on the head of the wearer to provide the optimum full angle and the optimum amount of force to form the desired fluid barrier between mask 12 and the face of the wearer.

Similarly, when in use with paneled mask body 212 shown in FIG. 12, tie straps 42 may extend from the corners of opening 66 to secure device 10 to the face of the wearer. Tie straps 42 work in association with the trapezoidal shape of the upper 62 and lower panels 63 to properly conform mask 212 around the nose, cheeks, and chin of the wearer. FIG. 11 illustrates the use of a single set of tie straps 42 which may be sufficient for use with a pre-formed cone mask 112.

Figure 5:
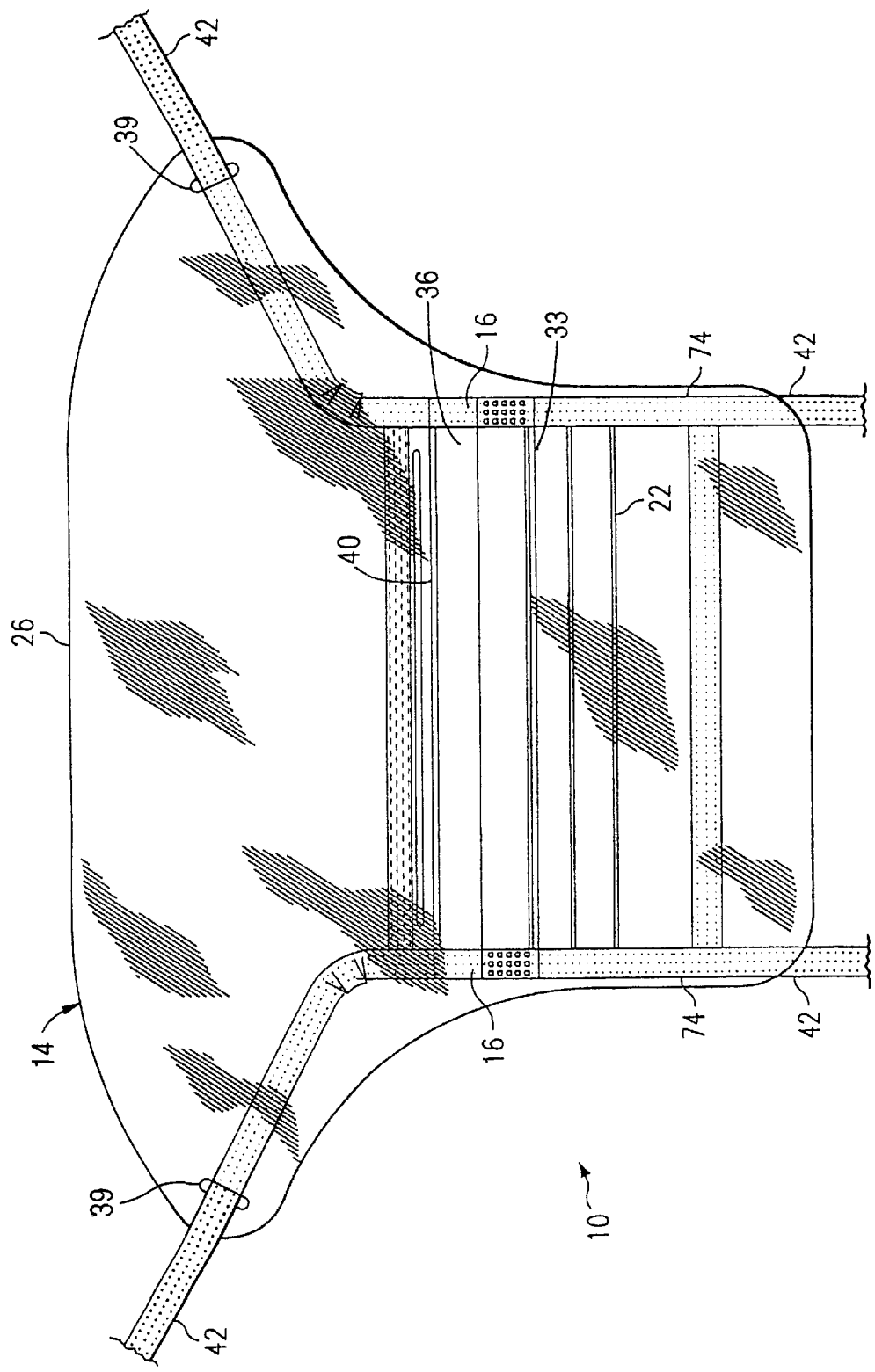
FIG. 5 is a front elevational view of one embodiment of a device for protecting the face of a wearer designed in accordance with the present invention.

As illustrated in FIGS. 2,5,9,11 and 12 shield 14 may be further secured to the head of the wearer by attaching tie straps 42 extending from the body of mask 12 to shield 14. In one embodiment, shown in FIGS. 2 and 12, the tie straps 42 may be bonded 58 to the lobe 28 of shield 14 to aid in conforming shield 14 along the sides of the wearer's face. Bonding may be accomplished by any one or a number of known techniques, including mechanical snaps, adhesive attachments, pressure sealing, ultrasonic sealing and heat sealing. Alternatively, tie straps 42 may be wound through openings or slits 39 as shown in FIGS. 5,9 and 11.

In use, a wearer holds protective device 10 up to his or her face. The wearer then places the mask 12 portion of the device 10 over the nose and mouth. The wearer can then pull, for example, tie straps 42 over the ears and behind the head to tie mask 12 in place. Pleats 22 or opening 66 in mask 12 will pull apart as tie straps 42 are pulled, conforming mask 12 to the face of the wearer. Malleable strip 20 is bent and shaped around the nose of the wearer as tie straps 42 are pulled, supporting the filtering medium of mask 12 away from the nose and mouth of the wearer. Shield 14, being attached to mask 12 at bond areas 16, is suspended in front of wearer's face. Arcuate lobes 28,38 of shield 14 can be bent backward along creased edges 76 to better protect the eyes of the wearer. Device 10 is thus properly worn by wearer, and the wearer can then safely perform designated tasks with eyes, nose, and mouth shielded from harmful or undesirable contaminants.

While preferred embodiments of the present invention have been described above, it is to be understood that any and all equivalent realizations of the present invention are included within the scope and spirit thereof. Thus, the embodiments depicted are presented by way of example only and are not intended as limitations upon the present invention. While particular embodiments of the invention have been described and shown, it will be understood by those of ordinary skill in this art that the present invention is not limited to such embodiments since many modifications can be made that are within the scope and spirit of the invention. Therefore, it is contemplated that any and all such embodiments are included in the present invention as may fall within the literal or equivalent scope of the appended claims.

What is claimed is:

1. A device for protecting the face of a wearer, the device comprising:
    a gas pervious mask having a body dimensioned to fit over the nose and mouth of the wearer; and
    a shield attached directly to said body of the gas pervious mask, the shield being at least partially transparent over the eyes of the wearer, the shield dimensioned to cover said body of the gas pervious mask and the eyes of the wearer.

2. The device of claim 1, wherein the shield is constructed of a liquid-impermeable, lightweight material.

3. The device of claim 1, wherein the gas pervious mask comprises a single layer of material.

4. The device of claim 1, wherein the gas pervious mask comprises at least two layers of material.

5. The device of claim 1, wherein the gas pervious mask includes a darkened anti-glare strip along a portion of the mask.

6. The device of claim 1, further comprising at least one strap attached to said body of the gas pervious mask for securing the gas pervious mask about the wearer's head.

7. The device of claim 1, wherein said body of the gas pervious mask is attached to the shield with sonic bonding.

8. The device of claim 1, wherein the shield comprises a non-reflective surface along at least a portion of the shield.

9. The device of claim 1, wherein the gas pervious mask includes at least one lateral pleat, the pleat conforming said body of the gas pervious mask to the nose and mouth of the wearer.

10. The device of claim 9, wherein the gas pervious mask includes a malleable strip located along a top edge of said body of the gas pervious mask parallel to the lateral pleat.

11. The device of claim 1, wherein said body of the gas pervious mask has two side edges, the shield being coupled to the gas pervious mask at bonding areas located on the side edges of the gas pervious mask, thereby permitting the gas pervious mask and the shield to separately conform to the face of the wearer.

12. The device of claim 1, wherein said body of the gas pervious mask has a front side and a center pleat formed in the front side, the shield being coupled to the mask by at least one bonding area located along the center pleat.

13. The device of claim 1, further comprising a strip of plastic film attached to a top edge of the mask above the nose and mouth of the wearer.

14. The device of claim 13, wherein the strip of plastic film further comprises an edge attached to the mask, and an opposite edge attached to the shield, and a fold lying between said edge and said opposite edge.

15. The device of claim 13, wherein the strip of plastic film further comprises an edge attached to the mask, an opposite edge attached to the shield, and a plurality of pleats lying between said edge and said opposite edge.

16. The device of claim 13, wherein the strip of plastic film is malleable.

17. The device of claim 1, the gas pervious mask further comprising:
    said body having an open end sized to cover the nose and mouth of the wearer and a closed end, said open end defined by a top edge and a bottom edge;

said top edge positioned to extend across the nose and cheeks of the wearer;

said bottom edge positioned to extend below the mouth of the wearer;

said top edge and said bottom edge having connecting opposite ends.

18. The device of claim 17, wherein the gas pervious mask has a center seam along the closed end, the shield being coupled to the mask by at least one bonding area located adjacent the center seam.

19. The device of claim 1, said body of the gas pervious mask further comprises a molded body having an opening shaped to cover the nose and mouth of the wearer.

20. The device of claim 19, wherein said body of the gas pervious mask has a front side, the shield being coupled to the mask by at least one bonding area located on the front side.

21. A device for protecting the face of a wearer comprising:

a gas pervious mask body dimensioned to cover the nose and mouth of the wearer, the gas pervious mask body generally conforming to the face of the wearer;

the gas pervious mask body having an opening generally shaped to encompass the nose, cheeks, and chin of the wearer defined in part by a top edge, and a bottom edge, and two opposite sides;

a shield coupled to the gas pervious mask body by at least one bond area, the shield being at least partially transparent and dimensioned to cover the eyes of the wearer and the gas pervious mask;

and the shield having a perimeter being greater in length than the perimeter of the gas pervious mask and extending beyond the perimeter of the gas pervious mask.

22. The device of claim 21, wherein the shield is shaped to have a bottom edge, a top edge, and two opposite sides, having an arcuate lobe extending from each side.

23. The device of claim 22, wherein the gas pervious mask further comprises at least one pair of tie straps coupled to said body for securing the gas pervious mask about the wearer's head.

24. The device of claim 23, wherein each of the tie straps extends from one side of the gas pervious mask and is coupled with the respective arcuate lobe of the shield.

25. The device of claim 23, wherein each arcuate lobe includes an opening through which one of said tie straps pass as the tie strap extends from the side edge of the mask around the head of the wearer.

26. The device of claim 21, wherein the gas pervious mask further comprises at least one ear loop coupled to said body for securing the gas pervious mask about the wearer's head.

27. The device of claim 21, wherein the shield is flat and flexible.

28. The device of claim 21, wherein the shield further comprises a main body and an arcuate lobe extending from each of two side edges.

29. The device of claim 28, wherein the shield further comprises a crease along each side edge between the main body and the arcuate lobe.

30. The device of claim 21, the gas pervious mask body having a generally rectangular shape and is further defined by side edges along the two sides.

31. The device of claim 30, having two bond areas generally located along respective side edges of mask with each bond area occupying a predetermined area along the respective side edge.

32. The device of claim 21, wherein the gas pervious mask body includes multiple layers of material.

33. The device of claim 32, wherein at least one layer of the gas pervious mask extends from the bottom edge of the mask body for covering the neck of the wearer.

34. The device of claim 21, the shield further comprising a lower portion and an upper portion overlapping the lower portion opposite the gas pervious mask body.

35. The device of claim 34, wherein the lower portion is opaque.

36. The device of claim 34, wherein the lower portion is formed of a draping material.

37. A method for making a device for protecting the face of a wearer comprising the steps of:

forming a gas-pervious mask having a body dimensioned to fit over the mouth and nose of the wearer and a perimeter defined by a top edge, a bottom edge, and two side edges;

forming an at least partially transparent shield being dimensioned to cover the gas pervious mask and the eyes of the wearer; and attaching the at least partially transparent shield directly to the gas pervious mask body using at least one predetermined bond area, thereby permitting the gas pervious mask body and the shield to separately conform to the face of the wearer, the perimeter of the shield extending beyond the perimeter of the gas pervious mask body.

38. The method of claim 37, wherein the bond areas attaching the shield to the mask are along the side edges of the mask body.

39. The method of claim 37, further comprising the step of forming an arcuate portion on the bottom edge of the shield.

40. The method of claim 37, further comprising the step of forming lobes extending from each side of the shield.

* * * * *